(12) United States Patent
Patel et al.

(10) Patent No.: US 6,549,214 B1
(45) Date of Patent: Apr. 15, 2003

(54) AUTOMATIC SCALING OF DISPLAY FOR IMAGE MANAGEMENT SYSTEM

(75) Inventors: Alpesh Patel, Schaumburg, IL (US); Bradley E. Koehn, Milwaukee, WI (US)

(73) Assignee: General Electric Company, Schnectady, NY (US)

( * ) Notice: Subject to any disclaimer, the term of this patent is extended or adjusted under 35 U.S.C. 154(b) by 0 days.

(21) Appl. No.: 09/476,619

(22) Filed: Dec. 31, 1999

(51) Int. Cl.[7] .................................................. G09G 5/00
(52) U.S. Cl. ........................ 345/660; 345/668; 345/1.1
(58) Field of Search ........................... 345/1.1, 3.1, 3.3, 345/3.4, 660, 667, 668, 669

(56) References Cited

U.S. PATENT DOCUMENTS 4,725,892 A * 2/1988 Suzuki et al. ............... 345/668
5,027,110 A * 6/1991 Chang et al. ................ 345/660
5,172,103 A * 12/1992 Kita ............................ 345/668
6,339,434 B1 * 1/2002 West et al. .................. 345/667

* cited by examiner

*Primary Examiner*—Matthew Luu
(74) *Attorney, Agent, or Firm*—Foley & Lardner; Peter J. Vogel; Michael A. Della Penna

(57) ABSTRACT

An image management system has an image database configured to store a plurality of image data files and a workstation coupled to the image database. The workstation includes a memory to store configuration data, a display, and a data processing device. The data processing device is configured to retrieve a selected image data file from the image database generate a scaling factor based on the configuration data, and generate a display signal based on the selected image data file and the scaling factor. The display is configured to receive the display signal and to generate indicia representative of the display signal.

21 Claims, 3 Drawing Sheets

AUTOMATIC SCALING OF DISPLAY FOR IMAGE MANAGEMENT SYSTEM

BACKGROUND OF THE INVENTION

This invention relates to image management systems, and more particularly to displaying an image on an image management system.

Medical scanners and medical imaging machines are an integral part of modern medical practice. These scanners and medical imaging devices utilize both electromagnetic radiation and sonic waves to produce images which are viewed by doctors for the diagnosis and care of patients. For example, ultrasound machines are useful for viewing fetuses during prenatal care in a pregnancy or blood flow patterns in arteries. Magnetic resonance imaging (MRI) machines are useful for producing images of a wide range of soft tissues.

In a large hospital, medical scanners and medical imaging devices are preferably networked with a central image database, such as a picture archival and communications system (PACS). The PACS is designed to provide a central storage for archive for medical images. Further, PACS is configured so that stored images may be retrieved. Typically, a hospital will have a single PACS that is networked with a plurality of medical scanners and medical imaging devices located throughout the hospital. Further, the PACS will be networked with a plurality of image workstations, such as a PACS workstation. Images generated by medical scanners and medical imaging devices are transferred to the PACS for storage and later retrieval and review by doctors located throughout the hospital at any of the plurality of image workstations.

The image workstations have one or more displays, each having a resolution (e.g., in dots per inch, or DPI). A multiple display system is advantageous for displaying a large amount of data all at once in order to maximize the efficiency of the radiologist or other operator. The displays present a graphical user interface to the operator which displays images retrieved images from the PACS, textual data (for example, from a radiology information system, or RIS), drop-down menus, icons, and other display elements, and which also receives operator input from a plurality of input devices (e.g., display buttons, voice recorders, etc.).

One drawback of having multiple workstations with multiple display resolutions occurs when the radiologist views an image at one workstation, then views the same or similar image at another workstation. If the first work station has a higher resolution (e.g., 168 DPI) than the second work station (e.g., 90 DPI), the image will appear smaller on the first work station than on the second. This can lead to confusion or misdiagnosis. Also, standard Microsoft Windows drop down menus, dialog boxes, and option boxes appear distorted between displays of varying resolution, further contributing to the confusion. Ideally, any indicia which is displayed on displays having various resolutions will appear the same in size and orientation.

It is a known procedure to download software to the workstation which is customized to include the resolution of the display used with the workstation. However, customized software is costly and lacks flexibility. For example, if a new display is coupled to the workstation, an entirely new software application must be loaded onto the workstation.

Therefore, there is a need for an image management system that automatically scales a display image based on the resolution of the display. Further, there is a need for a method of scaling a display of an image management system based on the resolution of the display. Such an image management system and method would not require customized software for each display. Such an image management system would also have the ability to determine its own hardware configuration and automatically make changes to the display data to conform to the hardware configuration.

SUMMARY OF THE INVENTION

According to one exemplary embodiment, an image management system has an image database configured to store a plurality of image data files and a workstation coupled to the image database. The workstation includes a memory to store configuration data, a display, and a data processing device coupled to the memory and the display. The data processing device is configured to retrieve a selected image data file from the image database, to generate a scaling factor based on the configuration data, and to generate a display signal based on the selected image data file and the scaling factor. The display is configured to receive the display signal and to generate indicia representative of the display signal.

According to another exemplary embodiment, a method of scaling a display of an image management system having a resolution includes: retrieving a selected image data file from an image database; generating a scaling factor based on the resolution; generating a display signal based on the selected image data file and the scaling factor; and providing the display signal to the display.

According to yet another exemplary embodiment, an image management system has a display with a resolution. The image management system includes a means for retrieving a selected image data file from an image database; a means for generating a scaling factor based on the resolution; a means for generating a display signal based on the selected image data file and the scaling factor; and a means for providing the display signal to a display.

According to still another exemplary embodiment, an image. management system has an imaging device configured to generate an image data file having resolution data representative of the resolution of the image data file and an image database coupled to the imaging device configured to store the image data file and the resolution data. The image management system further includes a workstation coupled to the image database the workstation having a display and a data processing device. The data processing device is coupled to the display and configured to retrieve the image data file and the resolution data from the image database, to generate a scaling factor based on the resolution data, and to generate a display signal based on the retrieved image data file and the scaling factor. The display is configured to receive the display signal and to generate indicia representative of the display signal.

BRIEF DESCRIPTION OF THE DRAWINGS

The invention will become more fully understood from the following detailed description, taken in conjunction with the accompanying drawings, wherein like reference numerals refer to like parts, in which.

DETAILED DESCRIPTION OF THE PREFERRED EMBODIMENTS

Figure 1:
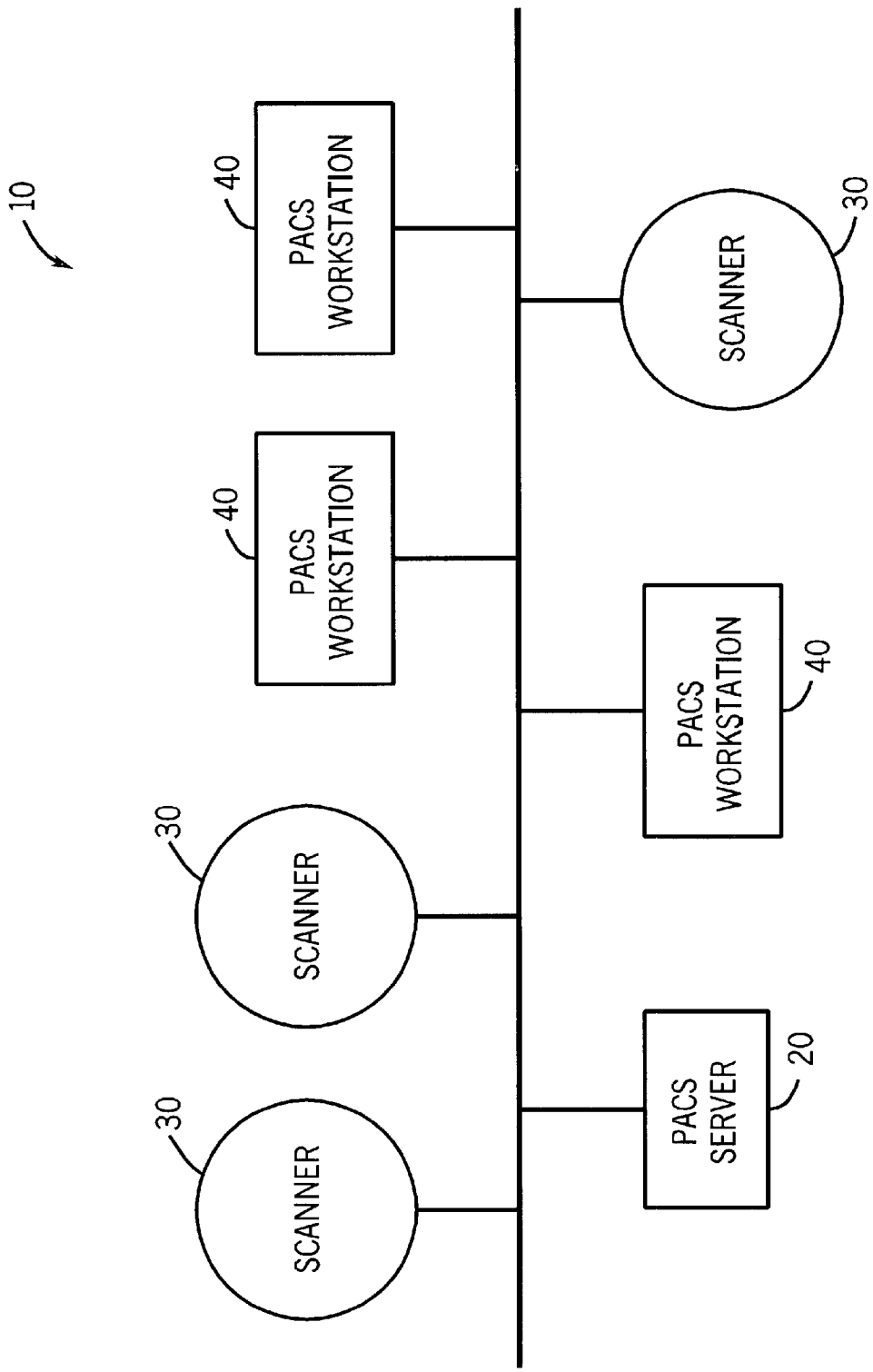
FIG. 1 is a block diagram of an image management system according to an exemplary embodiment.

Referring now to FIG. 1, a block diagram of an image management system 10 is depicted. Image management system 10 includes an image manager or database 20 which, in a preferred embodiment, is a picture archival and communication system (PACS) server (for example, a PATHSPEED server by General Electric Medical Systems). However, image database 20 is not limited to a PACS server, but may be any picture archiving apparatus. In a preferred embodiment, image database 20 includes an information storage unit (ISU) for short-term storage and retrieval and an archival storage unit (e.g., an optical disc storage and optical disc reader system) for long-term storage and retrieval. Image database 20 may also comprises hard disk storage.

Image database 20 is coupled to a plurality of imaging devices 30 which are configured to create digitized image data based on an image subject such as, but not limited to, portions of the human anatomy. In a preferred embodiment, imaging devices 30 include, but are not limited to, magnetic resonance imaging (MRI) devices, ultrasound imaging devices, computer tomography (CT) devices, nuclear imaging devices, X-ray imaging devices and any other types of imaging devices, not limited to the medical field. In a preferred embodiment, imaging devices 30 produce image data files in the DICOM3 or DEFF formats. However, other image data file formats are equally applicable. The image data files are communicated from imaging devices 30 to image database 20 and represent two-dimensional slices through the object being imaged. Therefore, from a single image data file stored on image database 20, a two dimensional image rendering may be reconstructed. Such two dimensional renderings are then presented to an operator on any of a number of workstations 40 that are coupled to communications network 22 (such as an Ethernet or other applicable communications network connection) that is in communication with image database 20. Workstations 40 may be, in an exemplary embodiment, a PACS workstation and operates a Microsoft Windows NT operating system.

Figure 2:
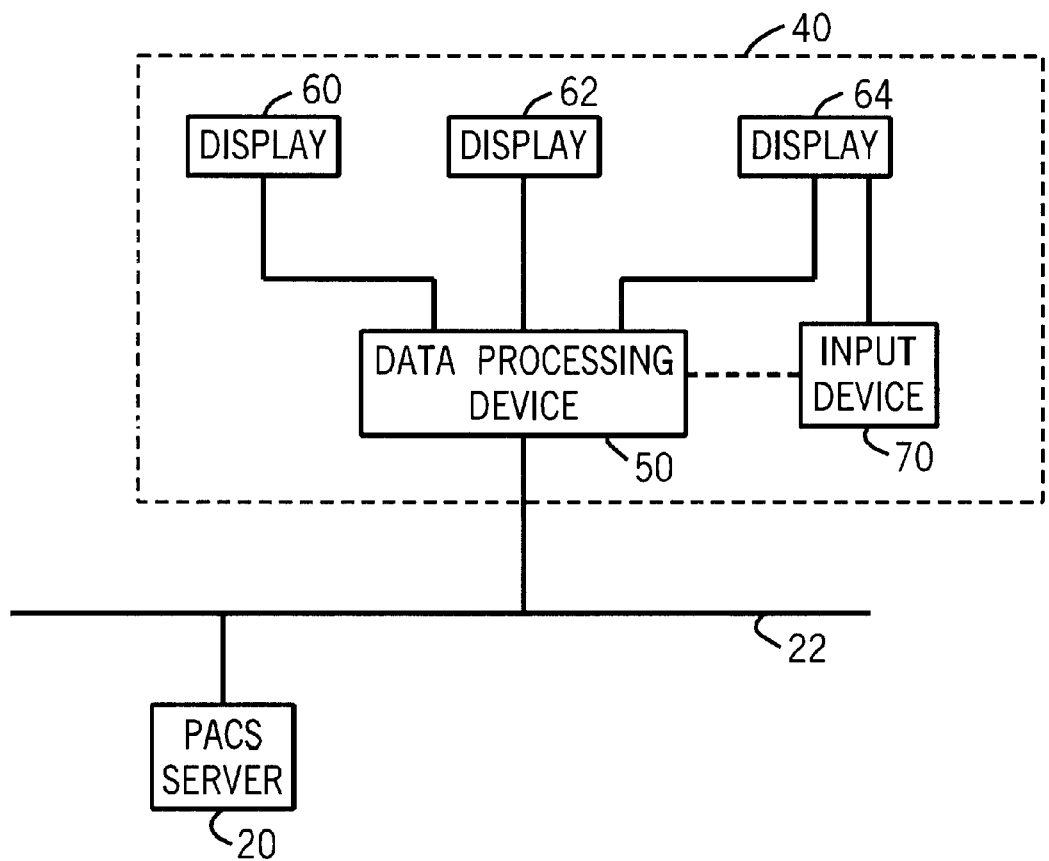
FIG. 2 is a block diagram of an image management system having a data processing device according to an exemplary embodiment.

Referring now to FIG. 2, a more detailed view of one of workstations 40 is shown comprising a data processing device 50 coupled to communications network 22 and a plurality of displays 60, 62, and 64, and an input device 70 which may be part of display 64, part of displays 60, 62, and 64, or coupled directly to data processing device 50. As mentioned, image database 20 stores a plurality of image data files. Data processing device 50 of workstation 40 includes a microprocessior and/or other processing circuitry (e.g., memory, communication circuitry, input/output devices, hard disk storage, etc.). Data processing device 50 is configured to receive and store a software application which an operator may run to view image data files from image database 20. The software application may be a Microsoft Windows NT-based application having various graphical user interface components. Data processing device 50 is also configured to store configuration data for workstation 40 including, for example, hardware configuration data, such as, display resolutions and the number of displays coupled to data processing device 50.

In this embodiment, displays 60, 62, and 64 all have the same resolution, which ranges between approximately 90 and 168 dots per inch (DPI), though greater and lesser resolutions are also contemplated herein. Data processing device 50 retrieves a selected image data file from the image database. For example, the selected image data file may be chosen by the operator via input device 70 (e.g., a keyboard, mouse, touch-screen, etc.). Data processing device 50 then generates a scaling factor for the image data based on the resolution of displays 60, 62, and 64. In this embodiment, the application running on data processing device 50 reads the resolution of displays 60, 62, and 64 from the configuration data stored in memory and references a scaling table in memory to determine the desired scaling factor. The scaling table includes a maximum resolution associated with a first scaling factor and a minimum resolution associated with a second scaling factor. If the resolution of displays 60, 62, and 64 is between the minimum and maximum resolutions, data processing device 50 interpolates linearly to determine the desired scaling factor. Other methods of determining the desired scaling factor based on the resolution of the displays are contemplated (e.g., a table with a set of predetermined scaling factors based on all possible display resolutions).

Data processing device 50 generates a display signal based on the image data file. The display signal is formatted, for example, according to the VGA, XVGA, RGB or other standard format. Data processing device 50 includes a graphical user interface in the display signal. Data processing device 50 scales the display signal having the image data file and the graphical user interface by the desired scaling factor determined as described above. To generate the display signal, data processing device 50 reads the number of displays (e.g., three in this example) from the configuration data and formats the display signal for the displays based on the number of displays. For example, a two-dimensional image of a human head may be divided into three portions and displayed on all three displays 60, 62, and 64 to provide improved detail to the operator. As another example, two-dimensional images of three different slices of the human head, or three slices from the same location but using a different imaging technique, may be displayed on each of the three respective displays 60, 62, and 64. As yet another example, if the display signal indicates a dialog box should be displayed, data processing device 50 generates the dialog box in each of the three displays 60, 62, and 64 so that the operator can quickly view the dialog box regardless of which of the three displays 60, 62, and 64 is being viewed at the time.

Displays 60, 62, and 64 are monitors, such as, a MGD 521 monitor manufactured by Barco, a DR9021 monitor manufactured by Dataray, a D2846 monitor manufactured by Hewlett Packard, or other monitors. Displays 60, 62, and 64 receive the display signal from data processing device 50 and generate operator-readable indicia representative of the display signal.

As mentioned, in prior art devices, if displays 60, 62, and 64 are replaced with displays of a different resolution, new customized software applications must be loaded into data processing device 50 (i.e., data processing device 50 must be completely reprogrammed) to support the new displays. In the present exemplary embodiment, however, data processing device 50 is configured to automatically scale the display signal. After a new monitor is installed, the operator operates input device 70 to command data processing device 50 to run a small program (e.g., a script) which determines the number and resolution of displays 60, 62, and 64 and stores the number and resolution of displays 60, 62, and 64 in the configuration data. Subsequently, the software application running on data processing device 50 may access the new configuration data and automatically apply the proper scaling factor to ensure a that the displayed indicia have the same size on displays 60, 62, and 64 as they did on the previous displays. Note that all other workstations coupled to communications network 22 may be likewise programmed so that an operator moving from one workstation display to the next workstation display sees similarly sized display items. Thus, in prior image management systems, each workstation ran customized software based on the number and resolution of the displays associated therewith. In the present exemplary embodiment, each workstation runs the same software which is flexible in design to accommodate multiple display resolutions and configurations.

According to a further feature, the operator may adjust the scale of the displayed image without affecting the scale of the graphical user interface (e.g., windows, dialog boxes, etc.) by using input device 70 to select from a plurality of additional scaling factors (e.g., 50%, 100%, 150%, etc.).

Figure 3:
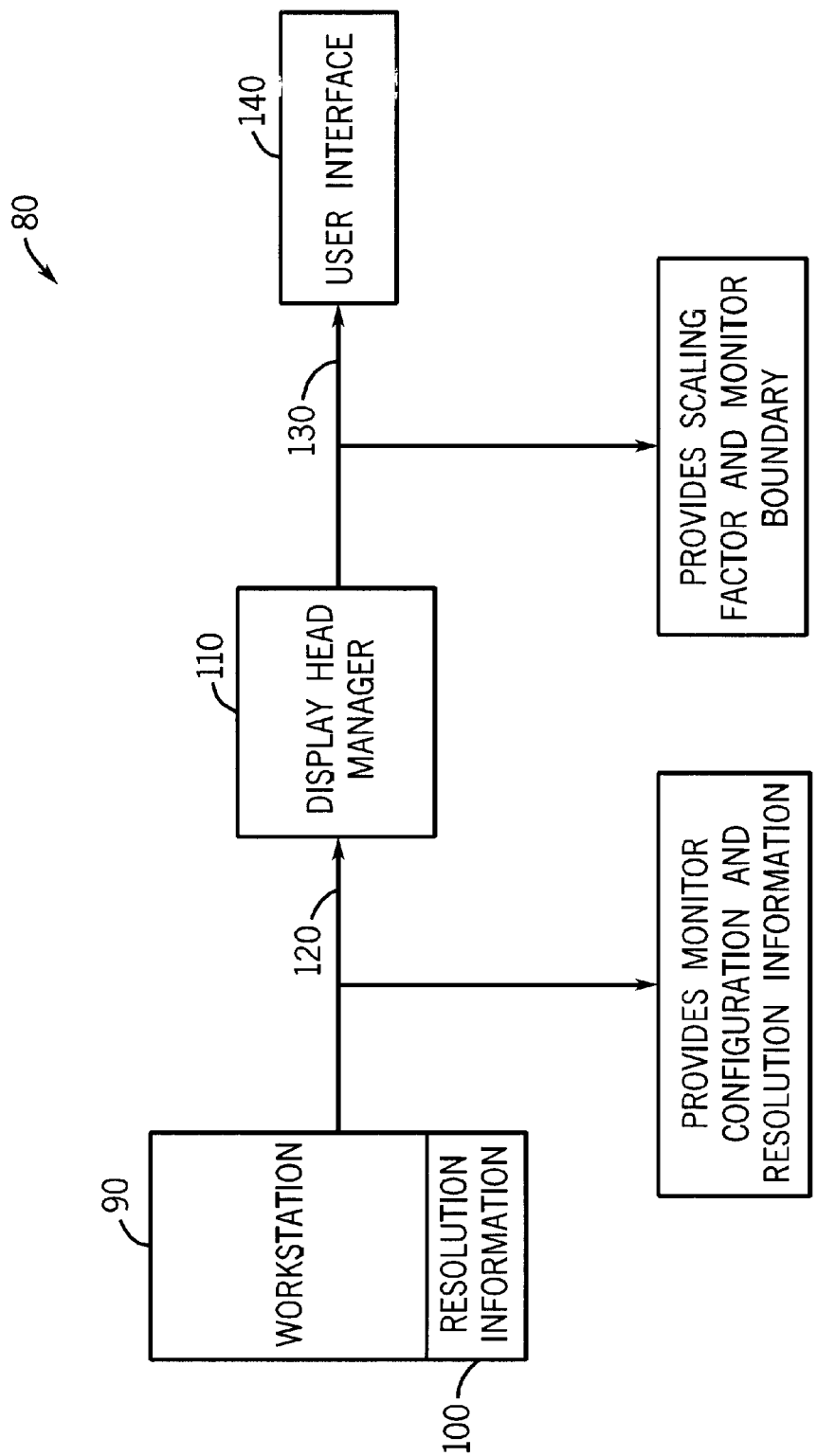
FIG. 3 is a flow diagram depicting steps in a method according to an exemplary embodiment.

Referring now to FIG. 3, a flow diagram 80 depicts steps in a method according to an exemplary embodiment. A workstation 90 includes a memory location 100 which stores configuration data (e.g., display configuration data, number of displays data, resolution data, etc.). Workstation 90 retrieves a selected image data file from an image database (not shown) and provides the selected image data file to a display head manager 110, as indicated by arrow 120. Workstation 90 also provides the configuration data to display head manager 110. Display head manager 110 is a software program operable on workstation 90 which generates a scaling factor based on the resolution data. Display head manager 110 may alternatively be a separate hardware module or other processing module. Display head manager 110 further generates a display signal by combining the image data file with a graphical user interface (e.g., a display boundary, icons, drop-down menus, and other display elements) and scaling the display signal by the scaling factor. The display signal is further modified based on the remaining configuration data (e.g., to accommodate multiple displays, etc.). As indicated by arrow 130, display head manager 110 provides the display signal to a display 140 (e.g., a monitor, a touch screen display, etc.).

While the preferred embodiment refers to imaging devices used in the medical area, the reference to imaging devices may be interpreted broadly. The embodiment can encompass those situations in which any imaging device is coupled to and in communication with a communications network and an image manager. An alternative example of an imaging device which generates image data is a digital camera. However, the resolution problem with digital cameras is compounded by the fact that these cameras create a broad range of image resolutions individually, and as a group. Thus, while the exemplary embodiment has been discussed in the context of displays with different resolutions, the present invention is also applicable to deviations in the resolution of image data.

Further, those who have skill in the art will recognize that the present invention is applicable with many different hardware configurations, software architectures, communications protocols and organizations or processes. Also, the present invention is applicable to systems which do not include an image database and merely display text and/or icons. In such an embodiment, the data processing device is configured to retrieve any desired display data, generate the scaling factor based on the display resolution, and scale the display data based on the scaling factor for subsequent display.

While the detailed drawings, specific examples, and particular formulations given describe preferred embodiments, they serve the purpose of illustration only. The materials and configurations shown and described may differ depending on the chosen performance characteristics and physical characteristics of the communications networks. For example, the type of communications network or communications protocols used may differ. The systems shown and described are not limited to the precise details and conditions disclosed. Furthermore, other substitutions, modifications, changes, and omissions may be made in the design, operating conditions, and arrangements of the preferred embodiments without departing from the spirit of the invention as expressed in the appended claims.

What is claimed is:

1. An image management system, comprising:
   an image database configured to store a plurality of image data files; and
   a workstation coupled to the image database, the workstation comprising:
      a first display having a resolution;
      a memory to store display resolution data representative of the resolution of the display and to store a set of scaling data associated with a set of resolutions; and
      a data processing device coupled to the memory and the display configured to retrieve a selected image data file from the image database, to generate a scaling factor based on the display resolution data and the set of scaling data, and to generate a display signal based on the selected image data file and the scaling factor, wherein the display is configured to receive the display signal and to generate indicia representative of the display signal.

2. The image management system of claim 1, wherein the image data files comprise medical data.

3. The image management system of claim 1, wherein the image database includes a picture archival and communications system database.

4. The image management system of claim 1, wherein the data processing device is further configured to generate the display signal based on the number of displays coupled to the data processing device.

5. The image management system of claim 1, wherein the resolution is between approximately 90 and 168 dots per inch.

6. The image management system of claim 1, wherein the data processing device is configured to generate the scaling factor by linear interpolation based on a predetermined maximum resolution and a predetermined minimum resolution from the set of scaling data.

7. The image management system of claim 1, wherein the data processing device is configured to generate the resolution data in response to a request received from an operator input device.

8. The image management system of claim 1, further comprising a second display coupled to the data processing device having the resolution.

9. The image management system of claim 1, further comprising a second workstation coupled to the image database, wherein the second workstation has a second display having a second resolution different than the first resolution, wherein the workstation and the second workstation operate the same software application.

10. A method of scaling a display of an image management system, the display having a resolution, comprising:
    retrieving a selected image data file from an image database;
    generating a scaling factor based on the resolution and a set of scaling data associated with a set of resolutions;
    generating a display signal based on the selected image data file and the scaling factor; and
    providing the display signal to the display.

11. The method of claim 10, further comprising generating resolution data representative of the resolution in response to a request received from an operator input device.

12. The method of claim 10, wherein the scaling factor is generated by linear interpolation based on a predetermined maximum resolution and a predetermined minimum resolution from the set of scaling data.

13. The method of claim 10, wherein the display signal is generated based on the number of displays in the image management system.

14. The method of claim 10, wherein the selected image data file comprises medical data.

15. An image management system having a display with a resolution, comprising:

means for retrieving a selected image data file from an image database;

means for generating a scaling factor based on the resolution and a set of scaling data associated with a set of resolutions;

means for generating a display signal based on the selected image data file and the scaling factor; and means for providing the display signal to a display.

16. The image management system of claim 15, further comprising means for storing a plurality of image data files coupled to the means for retrieving, the means for retrieving for retrieving the selected image data file from the means for storing.

17. The image management system of claim 15, wherein the resolution is between approximately 90 and 168 dots per inch.

18. The image management system of claim 15, further comprising input means for receiving a request from an operator and means for generating resolution data representative of the resolution of the display in response to receiving the request.

19. The image management system of claim 15, wherein the scaling factor is generated by linear interpolation based on a predetermined maximum resolution and a predetermined minimum resolution from the set of scaling data.

20. The image management system of claim 15, wherein the means for generating a display signal generates the display signal based on the number of displays in the image management system.

21. The image management system of claim 15, wherein the selected image data file comprises medical data.

* * * * *